United States Patent [19]

Weiss

[11] 3,931,316

[45] Jan. 6, 1976

[54] METHOD OF PREPARING O-METHYL-ISOUREA HYDROGEN SULFATE AND O-METHYL-ISOUREA SULFATE FROM CYANAMIDE

[75] Inventor: Stefan Weiss, Trostberg, Germany

[73] Assignee: Suddeutsche Kalkstickstoff-Werke AG, Trostberg, Germany

[22] Filed: Dec. 18, 1974

[21] Appl. No.: 533,870

[30] Foreign Application Priority Data
Aug. 10, 1974 Germany.............................. 2438585
Aug. 10, 1974 Germany.............................. 2438584

[52] U.S. Cl............................................ 260/564 E
[51] Int. Cl.²...................................... C07C 123/00
[58] Field of Search ................................ 260/564 E

[56] References Cited
UNITED STATES PATENTS
3,551,489  12/1970  Schaefer et al. ................ 260/564 E
3,670,022  6/1972  Schaefer.......................... 260/564 E Primary Examiner—Gerald A. Schwartz
Attorney, Agent, or Firm—Hans Berman

[57] ABSTRACT

O-Methyl-isourea hydrogen sulfate is prepared from cyanamide, methanol, and sulfuric acid in a yield of better than 90% when crystalline cyanamide is added to a mixture of sulfuric acid and methanol containing 50 – 150 parts by weight methanol per part sulfuric acid and holding the resulting composition at −10° to 20°C. The recovered O-methyl-isourea hydrogen sulfate is further converted to O-methyl-isourea sulfate with yields greatly exceeding 50%, and even 80%, by holding a mixture of approximately equimolar amounts of cyanamide and of the hydrogen sulfate in a liquid medium essentially consisting of methanol at 5° to 40°C until the O-methyl-isourea sulfate is formed and can be recovered.

11 Claims, No Drawings

METHOD OF PREPARING O-METHYL-ISOUREA HYDROGEN SULFATE AND O-METHYL-ISOUREA SULFATE FROM CYANAMIDE

This invention relates to O-alkyl urea derivatives, and particularly to a method of preparing the hydrogen sulfate and the neutral sulfate of O-methyl-isourea.

The mineral acid salts of O-methyl-isourea are important intermediates in the synthesis of guanidine derivatives. The seed disinfectant 1,17-diguanidino-9-azaheptadecane sesquisulfate is typical of such guanidine derivatives (see British Pat. No. 1,294,443). Others include 1,8-didiguanidino-octane and 1,10-diguanidino-decane (German published patent application 22 19 461, Reisbrand). O-Methyl-isourea sulfate was prepared heretofore from cyanamide, methanol, and sulfuric acid (J. Bello, Biochimica et Biophysica Acta 18, 448; C.A. 1956, 9297a) in yields of less than 50%, based on the cyanamide employed. Further applications find O-methyl-isourea-salts as methylating agents. O-methyl-isourea-sulfate reacts, for instance, with potassium iodide and with thiourea to the corresponding methylated products with surprisingly high yields.

An important object of the invention is the provision of a method which permits O-methyl-isourea sulfate to be prepared from cyanamide at much better yields than were available heretofore.

It has now been found that O-methyl-isourea hydrogen sulfate is readily prepared from cyanamide in yields of better than 90% when the cyanamide is added in crystalline form to a liquid mixture of concentrated sulfuric acid and methanol in a weight ratio of 50 to 150 parts methanol per 100 parts sulfuric acid, and the resulting composition is held at −10° to 20°C until the O-methyl-isourea hydrogen sulfate is formed. The latter then is reacted with an approximately equimolar amount of cyanamide in a liquid medium essentially consisting of methanol at 5° −40°C until the desired product is formed.

It is essential to good yields at favorable cost that the reaction mixtures not contain ingredients which later need to be removed by relatively complex steps in order to recover the desired products, and that diluents other than methanol be avoided throughout. Yet, it is necessary to hold the temperature of the reaction mixtures within the limits indicated above, and the requirements for close temperature control and highly concentrated reaction mixtures are generally contradictory and not readily met on an industrial scale.

It has been found that the reaction between cyanamide, methanol, and sulfuric acid to O-methyl-isourea hydrogen sulfate according to the equation

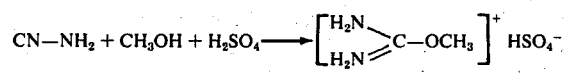

can be controlled readily and proceeds to very high yields of O-methyl-isourea hydrogen sulfate if the sulfuric acid and methanol are mixed first in a weight ratio of 50 to 150 parts methanol per 100 parts sulfuric acid, and the cyanamide is added to the liquid so obtained in crystalline form, the resulting composition being held at −10° to 20°C. It should contain a small excess of sulfuric acid over the cyanamide so that the mole ratio of cyanamide to sulfuric acid is preferably held between 1 : 1.05 and 1 : 1.4.

The reaction of cyanamide with the sulfuric acid and methanol is very rapid and exothermic. It is readily controlled by adding the cyanamide last to the other ingredients, and by using cyanamide in solid, particulate form. Agitation and external cooling in a conventional manner are adequate under these conditions to maintain the necessary temperature range in which secondary reactions and decomposition of the cyanamide are practically completely suppressed. Mixing of methanol and sulfuric acid, the term being employed to refer to the commercially available concentrated acid containing only minimal amounts of water, also liberates heat, and the use of a jacketed mixing vessel equipped with a stirrer is necessary unless better equipment is available. It is preferred to circulate methanol continuously between a mixing vessel and a heat exchanger, to add the sulfuric acid gradually to the contents of the mixing vessel, and to cool the mixture in the heat exchanger with refrigerated brine or another refrigerant.

For best results, the completed mixture of cyanamide, methanol, and sulfuric acid is held at temperatures as close to −10°C as the available cooling equipment permits to avoid side reactions. Highest yields are obtained under industrial conditions by stirring the mixture for two hours at −10° to 0°C after all ingredients are combined, and the generally preferred operating range of −10° to 10°C requires reaction times of four hours to 30 minutes, the time and temperature being inversely related, as is usual.

It is essential to the economic success of the process that the initial reaction mixture consist of nothing significant but cyanamide, methanol, and sulfuric acid. The impurities usually present in technical, crystalline cyanamide and the minute amounts of water present in concentrated sulfuric acid and technically anhydrous methanol do not significantly reduce the yield, but greater amounts of water decompose cyanamide in a known manner and correspondingly reduce the yield. The methanol and other ingredients of the reaction mixture remaining after recovery of the O-methyl-isourea hydrogen sulfate are readily recycled, and such recycling is facilitated by the absence of inert organic solvents.

O-Methyl-isourea hydrogen sulfate is soluble in methanol. Yet, it is recovered in solid form by precipitation from the concentrated reaction mixture, and the residual dissolved product is not lost when the liquid remainder of the reaction mixture is recycled and replenished to the desired ratio of the reactants of 37 to 47 parts by weight cyanamide and 75 to 100 parts methanol per 100 parts sulfuric acid, based on anhydrous $H_2SO_4$.

The slurry of crystalline O-methyl-isourea hydrogen sulfate in a liquid medium which results from the reaction is of surprisingly low viscosity and readily pumped through a heat exchanger to maintain its low temperature. It also yields the heat of reaction in a jacketed vessel equipped with a stirrer. The mother liquor may be recycled repeatedly before accumulated impurities and products of secondary reactions make it desirable to discard the filtrate or supernatant separated from the harvested crystals of O-methyl-isourea hydrogen sulfate. No recovery of methanol by distillation is necessary except from the ultimately discarded liquor.

The recycling method is readily performed in continuous apparatus. The product obtained in a very high yield is practically pure and ready for further reaction with cyanamide to neutral sulfate without further purification. The unavoidable losses of methanol by evaporation and leakage are insignificant because recovery of the solvent by distillation is not normally required.

O-Methyl-isourea sulfate is prepared from the hydrogen sulfate by reaction with cyanamide and methanol according to the equation

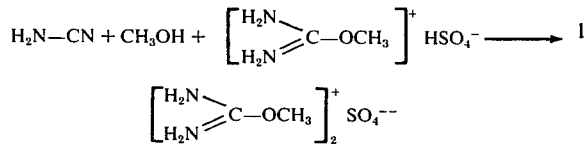

The reactants are converted to the desired neutral sulfate by holding a mixture of substantially equimolar amounts of the cyanamide and of the O-methyl-isourea hydrogen sulfate in a liquid medium essentially consisting of the methanol at a temperature of 5° to 40°C until the O-methyl-isourea sulfate is formed and can be recovered. Depending on the temperature chosen, maximum conversion may require 40 to 4 hours. At 30° to 40°C, the reaction period is 4 to 6 hours. The sequence in which the reaction partners are combined may affect the reaction period and the optimum reaction temperature. If cyanamide in solid form is added gradually to a solution of O-methyl-isourea hydrogen sulfate in methanol while the mixture is being stirred and cooled externally with cold water, excellent yields are achieved by stirring 20 hours at 18°C, the reaction time being increased at lower temperatures, reduced at higher ones.

A small excess of cyanamide over the O-methyl-isourea hydrogen sulfate initially present is often desirable. The methanol in the reaction mixture should amount to 40 to 100 parts by weight per 100 parts O-methyl-isourea hydrogen sulfate so that the mole ratio of cyanamide, O-methyl-isourea hydrogen sulfate, and methanol in the starting mixture is approximately 1 : 1 : 2–5. Adding a small amount sulfuric acid to the reaction mixture (0.05 to 0.1 mole per mole cyanamide) generally improves the yield of O-methyl-isourea sulfate.

The O-methyl-isourea sulfate generally precipitates from the liquid remainder of the reaction mixture in solid form. When this remainder is replenished to the desired mole ratio of the starting ingredients, an additional batch of O-methyl-isourea sulfate is obtained, and this recycling process may be repeated often enough to raise the yield to 80% or more, based on the O-methyl-isourea hydrogen sulfate consumed. Again, as described above with the synthesis of O-methyl-isourea hydrogen sulfate, the absence of inert organic solvents is important for the economic success of the process, and the relatively small amount of methanol in contact with the other reactants throughout the process of the invention makes it unnecessary to distill the solvent from the liquor from which the O-methyl-isourea sulfate was precipitated.

Because of the high concentration of cyanamide, sulfuric acid, O-methyl-isourea hydrogen sulfate in the several reaction mixtures of this invention, the apparatus required for a predetermined output is very compact, and floor space in production areas is used efficiently.

The following Examples are further illustrative of this invention. All parts and percentage values are by weight unless stated otherwise, and all temperatures are in degrees centigrade.

EXAMPLE 1

920 g 96% Sulfuric acid was added to 760 g methanol with stirring and external cooling of the mixing vessel at such a rate that the temperature of the solution did not exceed 5°C. Thereafter, the same temperature was maintained while 353 g crystalline 98% cyanamide was added with vigorous stirring. When all reactants were combined, stirring was continued for two hours at −10° to 0°C. The colorless, crystalline O-methyl-isourea hydrogen sulfate formed was filtered off with suction and dried in a vacuum at 40° to 50°C. It weighed 1187 g (84% yield).

The filtrate, weighing 609 g, was mixed with 300 g methanol and 875 g 96% sulfuric acid with stirring and cooling to a temperature not exceeding 5°C, and 353 g 98% crystalline cyanamide was stirred in at that temperature. Stirring was then continued for two hours at −10° to 0°C. The crystalline reaction product, when dried at 40° to 50°C in a vacuum, weighed 1354 g (96% yield).

The filtrate from the second batch of crystals was mixed with methanol, sulfuric acid, and cyanamide as described above to produce a third batch of O-methyl-isourea hydrogen sulfate, and the procedure was repeated twice more to produce a total of 6,588 g O-methyl-isourea hydrogen sulfate (93% yield). The mixed product had a melting point of 109° to 112°C and had a nitrogen content of 16.06% compared with a value of 16.27% calculated for $C_2H_8N_2O_5S$.

The use of 98% sulfuric acid instead of 96% sulfuric acid in the above mentioned example increased the yield by about 4 to 5%.

EXAMPLE 2

A solution of 915 g 96% sulfuric acid in 760 g methanol was prepared as in Example 1 and mixed with 353 g 98% cyanamide at 5°C, whereupon stirring was continued for three hours at −10° to 0°C. The reaction mixture than had an approximate viscosity of 450 centipoises at 5°C, as determined by means of a Brookfield viscosimeter. The solid O-methyl-isourea hydrogen sulfate was filtered off with suction, and the filtrate weighed 585 g. The wet solids on the filter were washed with 330 g methanol, and the separately collected washing liquor weighed 520 g. The crystalline material was dried in a vacuum at 45° to 50°C and weighed 969 g.

The filtrate and washing liquor were diluted with 150 g methanol and further combined with 353 g 98% cyanamide and 875 g 96% sulfuric acid in a manner obvious from the preceeding paragraph. After three hours of stirring at −10° to 0°C, the viscosity of the reaction mixture was about 300 centipoises at 5°C. It was worked up as above to recover 1193 g O-methyl-isourea hydrogen sulfate separately from 952 g filtrate and 484 g washing liquor.

The procedure described above was repeated several times in an identical manner except for a reduction of the methanol diluent to 30 g in subsequent cycles.

The total amount of colorless, crystalline O-methyl-isourea hydrogen sulfate recovered in five consecutive batches was 6,036 g (85.3% yield based on the cyanamide used). The product melted at 115° to 118°C and was found to contain 16.12% nitrogen.

EXAMPLE 3

To 172.2 g O-Methyl-isourea hydrogen sulfate (99% pure) mixed with 128 g methanol, 42.5 g 98% cyanamide was gradually admixed by stirring while the mixture was cooled externally with water of 11°C. After the ingredients had been combined, stirring was continued 30 minutes with water cooling and thereafter 20 hours at 20°C. The colorless, crystalline reaction product was filtered off with suction and dried in a vacuum at 40° to 50°C. The recovered crude O-methyl-isourea sulfate weighed 169 g (69.3% yield based on the original O-methyl-isourea hydrogen sulfate) and melted at 159° to 164°C. It contained 22.75% nitrogen, the exact amount calculated for $C_4H_{12}N_4O_2 \cdot H_2SO_4$.

When 20 hours stirring at 20°C in the above procedure was replaced by 5 hours of stirring at 30° to 35°C, the colorless, crystalline product weighed 166 g (68.1% yield), melted at 158° to 162°C, and contained 22.68% nitrogen.

The yield was improved to 73.0% (178 g) when 5 g 98% sulfuric acid was combined with the methanol solution prior to the 20 hours stirring period, and if water cooling was continued during the stirring. The product so obtained melted at 158° to 160°C and contained 22.50% nitrogen.

EXAMPLE 4

42.5 g 98% Cyanamide was added with stirring to a mixture of 172.2 g O-methyl-isourea hydrogen sulfate (99%) and 128 g methanol while the temperature was kept at 15° to 20°C. Stirring was continued at the same temperature for 18 hours after all ingredients had been combined. The colorless, crystalline O-methyl-isourea sulfate was recovered, and dried in a vacuum at 40°C. It weighed 168 g (68.9% yield), and 146 g filtrate was collected.

The filtrate was combined with 42.5 g 98% cyanamide, 40 g methanol, and 172.2 g O-methyl-isourea hydrogen sulfate (99%) and reacted as above, whereby a second batch of 204 g O-methyl-isourea sulfate (83.7% yield) was obtained. The mother liquor from the second batch was further processed in the same manner as the filtrate from the first batch, and a third mother liquor was used for producing a fourth batch of the desired product. The yield increased with each repetition of the processing cycle to reach 91.5% in the fourth batch.

The total amount of O-methyl-isourea sulfate was 801 g (82.1% yield), and the colorless crystals melted at 152° to 156°C. They contained 22.70% nitrogen.

EXAMPLE 5

600 g O-Methyl-isourea hydrogen sulfate (99%) and 445 g methanol were mixed with stirring and external cooling with 150 g 98% solid, particulate cyanamide at a rate to hold the temperature at 8° to 10°C, and stirring thereafter was continued at the same temperature for 40 hours. The reaction mixture was cooled to −10°C and centrifuged. The recovered colorless, crystalline material was dried at 40°C and weighed 682 g (81.2% yield). It was identified as O-methyl-isourea sulfate by its melting point of 155° to 160°C and its nitrogen content of 22.90%.

While the O-methyl-isourea hydrogen sulfate employed in Examples 3 to 5 was the dried product prepared by one of the methods of Examples 1 and 2, it is not normally necessary to dry or even to wash the crystalline O-methyl-isourea hydrogen sulfate precipitated from the reaction compositions of Examples 1 and 2 before further processing it to O-methyl-isourea sulfate in the steps exemplified by Examples 3 to 5. It is desirable, however, that the crude product recovered in Examples 1 and 2 by filtering or centrifuging be separated from the bulk of the liquid remainder of the reaction composition. For producing purest O-methyl-isourea sulfate, it is preferred that the O-methyl-isourea hydrogen sulfate be separated from substantially the entire liquid remainder of the reaction composition before being used for making the neutral sulfate.

What is claimed is:

1. A method of preparing O-methyl-isourea sulfate of the formula

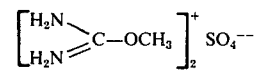

which comprises holding a mixture of substantially equimolar amounts of cyanamide and O-methyl-isourea hydrogen sulfate of the formula

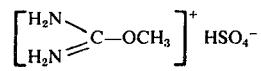

in a liquid medium essentially consisting of methanol at a temperature of 5° to 40°C for a period sufficient for forming said O-methyl-isourea sulfate, and recovering the formed O-methyl-isourea sulfate from said medium.

2. A method as set forth in claim 1, wherein said period extends for 4 to 40 hours.

3. A method as set forth in claim 2, wherein the amount of said methanol in said medium is 2 to 5 moles of methanol per mole of said cyanamide.

4. A method as set forth in claim 1, wherein said medium further includes sulfuric acid in an amount of 0.01 to 0.1 mole per mole of said cyanamide.

5. A method as set forth in claim 1, wherein said temperature is 30° to 40°C, and said period is 4 to 6 hours.

6. A method as set forth in claim 1, wherein said mixture is held at said temperature in said medium until said O-methyl-isourea sulfate is formed in an amount exceeding 50 mole percent of said O-methyl-isourea hydrogen sulfate.

7. A method as set forth in claim 1, wherein said O-methyl-isourea hydrogen sulfate, prior to said holding of said mixture, is prepared by mixing concentrated sulfuric acid with methanol in a weight ratio of 50 to 150 parts methanol to 100 parts sulfuric acid, and further with crystalline cyanamide, and holding the resulting composition at −10° to 20°C until said O-methyl-isourea hydrogen sulfate is formed.

8. A method as set forth in claim 7, wherein the weight of said crystalline cyanamide is 37 to 47 parts per 100 parts of said sulfuric acid, on an anhydrous basis, the weight of said methanol being 75 to 100 parts, said methanol and sulfuric acid being mixed, and said cyanamide being added to the mixed sulfuric acid and methanol.

9. A method as set forth in claim 7, wherein said formed O-methyl-isourea hydrogen sulfate is separated from substantially the entire remainder of said composition prior to said holding of said mixture.

10. A method as set forth in claim 9, wherein said remainder is replenished with at least one member of the group consisting of cyanamide, sulfuric acid, and methanol until the replenished composition contains, per 100 parts of said sulfuric acid on an anhydrous basis, 37 to 47 parts of said cyanamide and 75 to 100 parts of said methanol.

11. A method of preparing O-methyl-isourea hydrogen sulfate which comprises mixing concentrated sulfuric acid and methanol in a weight ratio of 50 to 150 parts methanol to 100 parts sulfuric acid, adding crystalline cyanamide to the liquid so obtained, holding the resulting composition at −10° to 20°C until said O-methyl-isourea hydrogen sulfate is formed, and separating the formed O-methyl-isourea hydrogen sulfate from the bulk of the remainder of said composition.

* * * * *